US006562012B1

(12) United States Patent
Brown et al.

(10) Patent No.: US 6,562,012 B1
(45) Date of Patent: May 13, 2003

(54) APPARATUS AND METHOD FOR MEASURING DROP SIZE IN AN INTRAVENOUS DRIP CHAMBER

(75) Inventors: Houston Brown, Poway, CA (US); C. William Barnes, Murrieta, CA (US)

(73) Assignee: Alaris Medical Systems, Inc., San Diego, CA (US)

( * ) Notice: Subject to any disclaimer, the term of this patent is extended or adjusted under 35 U.S.C. 154(b) by 0 days.

(21) Appl. No.: 09/717,437

(22) Filed: Nov. 20, 2000

(51) Int. Cl.⁷ .............................. A61M 5/00; A61M 5/14
(52) U.S. Cl. ............................. 604/253; 128/DIG. 13; 73/861.12
(58) Field of Search ............................. 604/251, 252, 604/253, 254, 255, 256, 246, 65, 66; 128/DIG. 13; 73/861.08, 861.11, 861.12

(56) References Cited

U.S. PATENT DOCUMENTS

| | | | |
|---|---|---|---|
| 3,390,577 A | 7/1968 | Phelps et al. ................. 73/194 |
| 3,450,153 A | 6/1969 | Hildebrandt et al. ........ 137/486 |
| 3,500,366 A | 3/1970 | Chesney et al. ............ 340/222 |
| 3,545,271 A | 12/1970 | Amir et al. .................... 73/194 |
| 3,553,583 A | 1/1971 | Wiley ......................... 324/189 |
| 3,641,543 A | 2/1972 | Rigby ......................... 340/239 |
| 4,105,028 A | * 8/1978 | Sadlier et al. ....... 128/DIG. 13 |
| 4,137,940 A | * 2/1979 | Faisandier .................. 137/486 |
| 4,173,224 A | * 11/1979 | Marx et al. .......... 128/DIG. 13 |
| 4,237,878 A | 12/1980 | Kobayashi et al. ......... 128/214 |
| 4,432,761 A | * 2/1984 | Dawe .......................... 222/420 |
| 4,583,975 A | 4/1986 | Pekkarinen et al. ........ 604/253 |
| 4,710,757 A | 12/1987 | Haase ......................... 340/684 |
| 5,125,265 A | 6/1992 | O'Connell et al. ........ 73/61.41 |
| 5,135,485 A | 8/1992 | Cohen et al. ................. 604/67 |
| 5,152,424 A | 10/1992 | Weinreb et al. ................ 222/1 |
| 5,186,057 A | 2/1993 | Everhart .................. 73/861.41 |

FOREIGN PATENT DOCUMENTS

| GB | 1221568 | 2/1971 | |
|---|---|---|---|
| WO | WO 00/42394 | 7/2000 | ............. G01F/3/00 |

* cited by examiner

*Primary Examiner*—Manuel Mendez
*Assistant Examiner*—Mark Han
(74) *Attorney, Agent, or Firm*—Fulwider Patton Lee & Utecht, LLP

(57) ABSTRACT

A capacitive-based apparatus for measuring the volume of a fluid drop passing through an intravenous drip chamber. The apparatus includes a capacitor comprising two parallel plates that are a fixed distance apart and are positioned such that the fluid flow path in the drip chamber is between them. The fluid drop moving through the drip chamber between the plates causes the capacitance of the plates to change. This change in capacitance is measured and from it, the volume of the drop is calculated. The volumes of a series of drops are integrated to provide a measured rate of flow through the drip chamber. This measured rate of flow is compared to the programmed rate of flow and the difference is used to adjust a flow control device to obtain the desired rate of flow. The measured flow rate is also displayed.

27 Claims, 2 Drawing Sheets

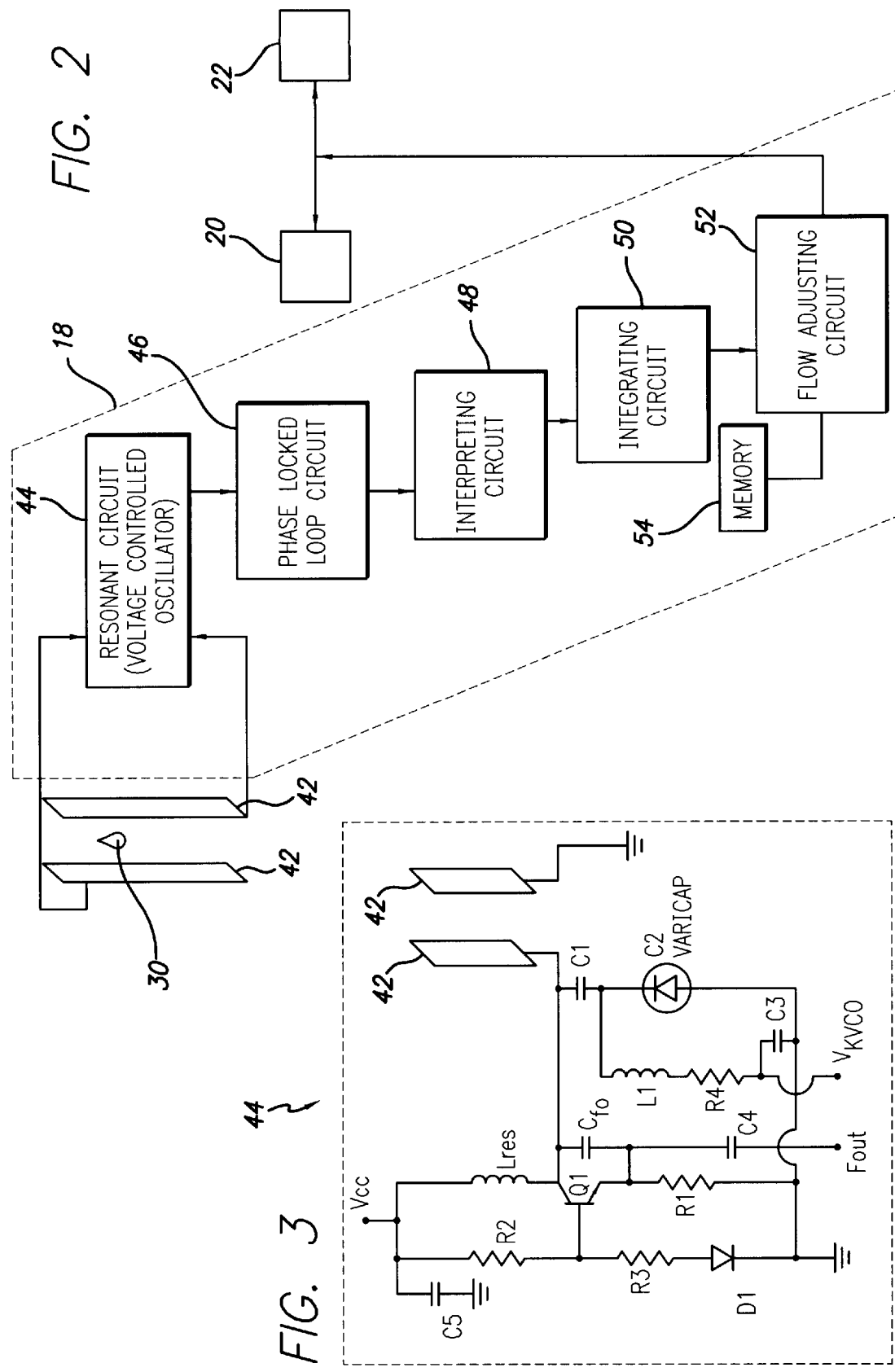

APPARATUS AND METHOD FOR MEASURING DROP SIZE IN AN INTRAVENOUS DRIP CHAMBER

BACKGROUND

The present invention relates generally to an apparatus and method for measuring fluid volume, and more particularly, to an apparatus and method that measures the volume of a drop of fluid falling through free space.

Conventionally, in an intravenous (hereafter "IV") infusion apparatus, an aqueous solution of medication in an inverted bottle, or other type of fluid reservoir, is supplied to a patient through a fluid administration set comprising tubing, a cannula for insertion into the patient's blood vessel, various fluid control devices such as clamps, injection sites, and at the upstream end, a drip chamber device. The drip chamber device includes a drop former at its upstream end, a transparent chamber through which drops are to fall, and an outlet port at its downstream end. The drop former portion is typically constructed to form drops having a predetermined volume. It has become typical for a drip chamber manufacturer to specify that a particular number of drops equals a particular volume of fluid. For example, a drop former may be constructed such that 20 drops equals a milliliter. As the fluid is supplied to the drip chamber from the fluid reservoir, the drop former generates drops of the fluid that fall through the transparent chamber to the outlet port. The very existence of drops indicates that fluid is flowing in the fluid administration system. The falling drops can be visibly observed in the transparent chamber and counted over a unit of time to calculate the flow rate. The flow rate can be adjusted by a clamp or other device upstream of the drip chamber device, or by downstream means such as an infusion pump. If an infusion pump is used, it will engage the administration set downstream of the drip chamber device and can be used to set a flow rate. The frequency of drops through the drip chamber will then depend on the flow rate set at the infusion pump.

A need exists for a reliable system that can more accurately measure the rate of flow of infusion medication through a fluid administration set. Typically, a treatment fluid is prescribed at a particular flow rate for a patient. Staying at that flow rate is desired so that the prescribed treatment is delivered. In the case where a transparent drip chamber is used, an upstream valve or clamp can be adjusted to control the rate of flow. Drops are observed in the drip chamber and are counted in an effort to monitor that the prescribed flow rate has been set. However, there are many factors that tend to cause the rate of flow to change after it has been initially set. For example, the rate of drop formation is dependent on the head height/pressure of the fluid reservoir. Depletion of the fluid supply will decrease the head pressure on the drop former and will cause a diminution in the rate of drop formation and flow. Vibration or shock may cause the rate controlling clamp to change its adjustment. An obstruction may find its way into the drop former causing the formation of smaller drops thus changing the rate of fluid flow. Uneven pumping by a downstream infusion pump can also cause variances in the frequency and shape of the drops. It would be helpful to make it readily known when a change in the rate of flow has occurred so that restoration of the desired flow rate can be effected.

As another consideration, the flow rate is typically determined by counting the number of drops per unit time and then performing a calculation to determine the actual flow rate. For example, if forty drops are counted in a time period of one minute, and the specification of the drip chamber is that twenty drops equals one milliliter, then the calculation is that a flow rate of two milliliters per minute exists. Should the actual volume in a drop vary from that specified for the particular drip chamber device, the actual fluid flow rate to the patient may be different from that calculated. This would likewise be undesirable as the patient would not be receiving the prescribed fluid flow.

Monitoring the flow rate through visual observation of drops as described above usually requires personal monitoring of the infusion by a nurse or other medical personnel. Infusions typically extend over a long period of time and this need for monitoring therefore represents a considerable problem to hospital personnel, especially when nurses are in short supply. The need to time drops over several minutes to determine the flow rate may occupy a significant amount of a nurse's time thereby leaving less time to perform other duties. A need to return numerous times during a lengthy infusion to again count drops also results in an increased demand on nurses whose schedules are already typically very busy.

Approaches for automating the monitoring process have been provided in the past. Many attempts have been made at providing an automated drop counter. While such systems have proved useful, they do not indicate by direct measurement the actual volume of the fluid detected. They only indicate that a drop has been detected. Such automated systems then use the drop volume as specified by the manufacturer of the drip chamber to determine volume. As discussed above, this may not always be accurate.

One prior approach is optical in nature and includes an array of photo detectors used to determine the size of the shadow of a drop as it passes in front of the detector. However, the variability of the optical qualities of drip chambers has posed a difficult obstacle to overcome. Also, condensation in the drip chamber can interfere with accuracy of an optical system as can intense room lighting. Another environmental condition that has impacted the usefulness of optical systems is the tilting of the drip chamber so severely that the drops may only partially pass across the photo detector. Further, the shape of drops varies from drop to drop. Those techniques that measure only one or two linear dimensions of a drop to determine its volume can have less than desirable accuracy due to this change in drop shape. It has been noted that a system that measures only one linear dimension of a drop, such as only length, to determine the drop volume can miscalculate the volume of the drop by thirty percent or more. Other optical methods have also been less accurate than desirable due to one or more of the above reasons.

Another method, as disclosed in U.S. Pat. No. 4,583,975 to Pekkarinen et al., is based on the piezoelectric effect. This system includes a piezoelectric film mounted to the inner wall of a drip chamber beneath the surface of accumulated fluid in the chamber. As a drop impinges on the surface of the accumulated fluid, the piezoelectric element is stressed and a voltage differential signal is generated. The method comprises the direct contact of an electric element of an electric circuit with the accumulated fluid in a drip chamber; fluid that may be in direct contact with a patient during an infusion thereby making this an undesirable approach for multiple reasons.

Another technique uses capacitive-based sensors to approximately determine the rate of fluid flow within a drip chamber. However, these methods are used only to detect the existence of a drop. They allow determination of the frequency of the drops, and rely upon the manufacturer's specified drop volume and an assumed constant drop volume to calculate the rate of flow. They do not take measurements sufficient to allow the actual volume of a drop itself to be determined. Further examples of capacitive-based sensors found in the prior art take measurements that allow determination of the accumulated fluid level in a drip chamber, from which flow rates may be determined, but do not take measurements from which the actual volume of a drop itself may be determined.

Although increased accuracy in fluid flow measurement is desired, cost is always a concern. The ability to make better health care available to an increasing number of people demands that the costs be kept as low as possible. It is desirable to lower the costs of medical devices so that they are affordable to a greater number of people.

Hence those skilled in the art have recognized a need for a fluid flow measurement device that is more accurate. A need has also been recognized for a flow sensing system that is insensitive to the shape of drops and is also insensitive to the optical characteristics of those drops. There has also been recognized a need to determine the volume of drops in a drip chamber so that an actual flow rate can be more accurately monitored. There is also a need for such a flow measurement device that is easier to manufacture and easier to use. The present invention fulfills these needs and others.

SUMMARY OF THE INVENTION

Briefly, and in general terms, the present invention is directed to a capacitive-based sensor for measuring the volume of a fluid drop passing through an IV drip chamber. The sensor includes a capacitor comprising two parallel plates which are a fixed distance apart and are positioned on either side of a drip chamber. The plates are positioned such that a fluid drop falls through the space between the plates, thereby causing the capacitance provided by the plates to change. This change in capacitance is measured and based on that sensed change in capacitance, the volume of the drop is more accurately calculated.

In one aspect, the change in capacitance is measured by incorporating the parallel plates into a resonant circuit having a resonant frequency dependent on the capacitance of the parallel plates. Any change in the resonant frequency of the circuit, as would be induced by a change in the capacitance of the parallel plates is detected and measured. The capacitance change is determined from the frequency change in the resonant circuit. In another aspect in accordance with the invention, the parallel plates may be part of a capacitive balanced bridge circuit, which experiences a change in capacitance when a fluid drop falls between the plates.

In both of the above-described aspects, the change in capacitance of the plates resulting from a drop falling between them is used to calculate the volume of the drop. The method of the present invention has the advantage of directly measuring the volume of each drop, thus eliminating the disadvantage of having to assume a drop size or shape. Moreover, the optical qualities of the drip chamber have no effect on the determination of the drop volume, thus eliminating a troublesome aspect of prior art methods which rely on optical methods to calculate drop size.

In another aspect, the present invention includes an electronic circuit which records the measured volume of each drop of a series of drops falling through an IV drip chamber over a period of time and integrates the result, thereby permitting measurement of the fluid flow rate through the drip chamber. In a further aspect, the present invention includes an electronic circuit which enables the device of the present invention to adjust the actual rate of flow through the drip chamber, based on the measured rate of flow.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 2 exemplifies the electronic circuitry of FIG. 1 in more detail.

FIG. 3 exemplifies a preferred embodiment of a resonant circuit having a resonant frequency and incorporating capacitive plates disposed about the drip chamber as shown in FIG. 1, wherein the resonant circuit is shown connected to a phase locked loop circuit with which the resonance frequency of the resonant circuit may be compared.

DETAILED DESCRIPTION OF THE PREFERRED EMBODIMENTS

Figure 1:
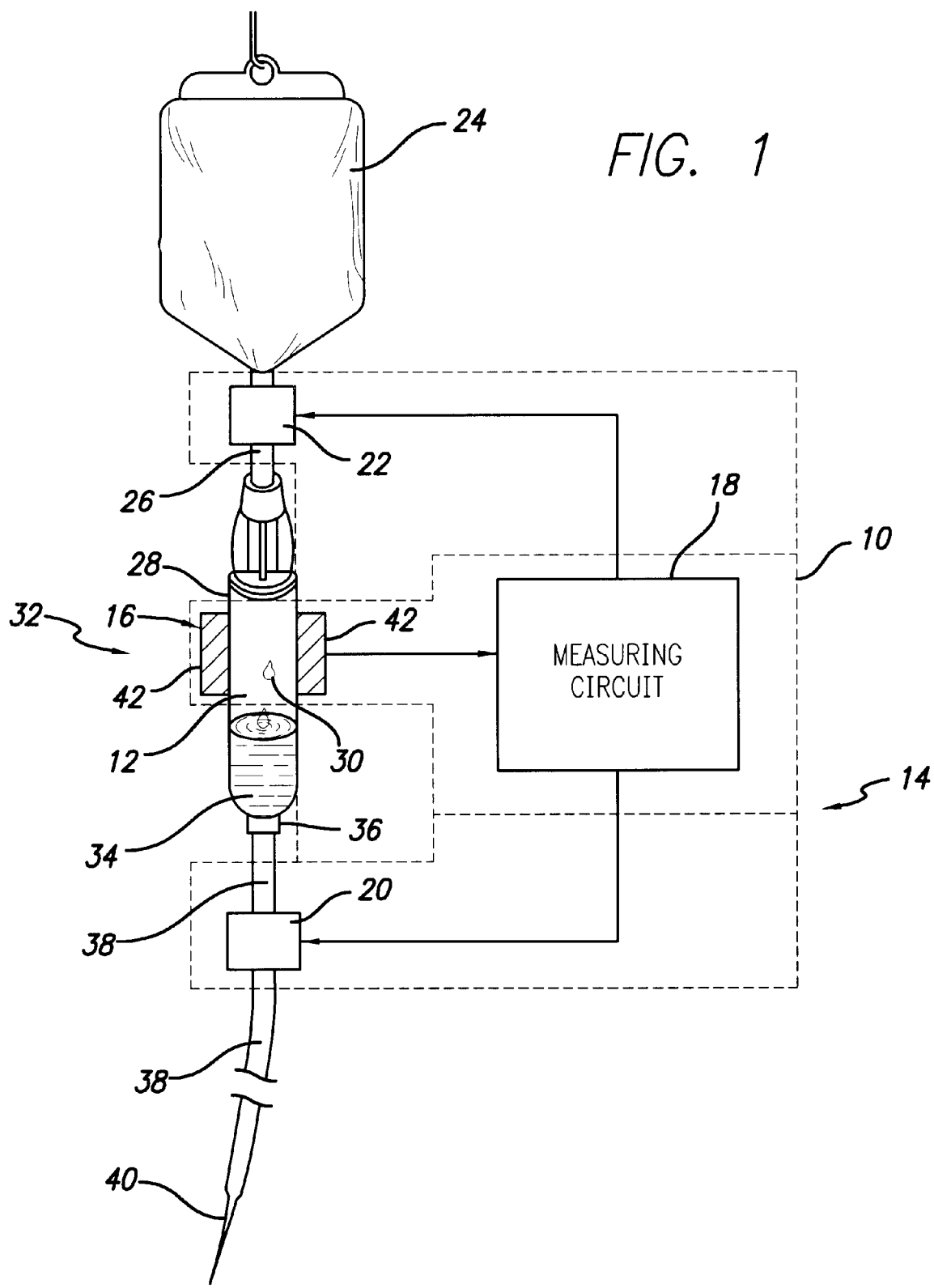
FIG. 1 exemplifies apparatus for controlling the flow of fluid to a patient in accordance with aspects of the invention, and more particularly, shows a conventional drip chamber with apparatus and electronic circuitry used to measure the volume of a drop falling within the drip chamber in accordance with more particular aspects of the invention.

Referring now to the drawings in detail, in which like reference numerals indicate like or similar elements among the several views, FIG. 1 shows a system 10 for measuring drop size in an intravenous drip chamber 12. Also shown is the measurement system 10 forming a part of a flow control system 14 where the flow is adjusted in accordance with the measurement system 10. The measurement system 10 in FIG. 1 comprises a sensor 16 mounted to the drip chamber 12 and a measuring circuit 18 that determines the volume of a drop in one embodiment and a flow rate in another embodiment.

In the flow control system 14, the measurement system 10 is included along with a flow control device 20, such as a peristaltic infusion pump. The output of the measurement system 10 is used by the flow control system 14 to control the downstream flow control device 20 to achieve a programmed flow rate. At the upstream end, a medical fluid reservoir, which in this case is a bag 24, is positioned so as to feed medical fluid via a conduit 26 into the drip chamber 12. Between the bag 24 and the drip chamber 12 in this embodiment is positioned an upstream flow control device 22. In one embodiment, an upstream flow control device 22 may comprise an electrically-controlled clamp. An upstream flow control device 22 may be used in place of or in addition to the downstream flow control device 20. The output of the measuring system 10 may also be used by the flow control system 14 to achieve a programmed flow rate. In the typical case however, only a downstream flow control device 20 would be used.

After the medication has passed through the upstream flow control device 22, it flows into the drip chamber 12 where an integral drop former at the upstream end 28 forms drops 30 of the medication whose path of fall is within a transparent enclosure 32 of the drip chamber. The drops of fluid collect at the downstream end 34 of the drip chamber 12 where there is located an output port 36. From the output port, the fluid flows downstream through a conduit 38, through a downstream flow control device 20, such as a large volume infusion pump, and through a cannula 40 into the vasculature of a patient.

The sensor 16 in this embodiment includes two parallel, electrically conductive metal plates 42 that are fixed at a constant distance apart and that define a capacitor. In one embodiment of the invention, the plates are installed outside the drip chamber 12 in fixed positions relative to the drip chamber, while in another embodiment the plates may be incorporated into the wall of the drip chamber.

In the embodiment of FIG. 1, one object of the capacitor formed by the two plates 42 is to measure the volume of a drop 30, count the drops per unit of time, and accurately determine a flow rate, as is discussed in more detail below. The size and shape of the plates 42 may vary depending on the application. In one embodiment, the plates 42 are curved and extend along a certain arc around the drip chamber 12.

It is preferable to not obscure the entire transparent enclosure 32 of the drip chamber 12, but to retain a transparent portion 32 thereof so that the nursing staff can still visibly check for the presence of drops. The height of the plates 42 is chosen in this embodiment to be longer than a drop so that an entire drop will fit between their top and bottom edges, but not long enough to encompass two or more drops at the highest flow rate. Further, the plates 42 should be located far enough below the drop former so that the drop is completely detached from the drop former before it enters the area between the plates 42. The plates should also be far enough above the fluid collecting at the downstream end of the drip chamber 12 so that any splashes made by the drops will not enter the area between the plates.

The measuring circuit 18 shown in FIG. 1 is configured, as explained more fully below, to take measurements that will allow the volume of a fluid drop falling between the plates 42 to be calculated. In this embodiment, even a small sphere of fluid falling from a drop former will cause a noticeable change in capacitance of the capacitor formed by the plates 42. More particularly, a drop of fluid that is introduced between the two electrically charged parallel plates set a fixed distance apart, d, from each other and separated by air so as to define a capacitor, will cause the capacitance of the plates to undergo a change, $\delta C$, which is approximately in direct proportion to the volume, $\Phi$, of the fluid drop according to the expression, $$\delta C \approx \frac{3\Phi\varepsilon_0}{d^2} \qquad \text{(Equation No. 1)}$$

where $\varepsilon_0$ represents the permittivity of free space. As used herein, the symbol "$\approx$" represents approximate equality. Because the space "d" between the plates 42 is fixed, $\varepsilon_0$ is known and $\delta C$ and $\Phi$ are the only variables, the volume of a drop of fluid $\Phi$ can be calculated if the change in capacitance $\delta C$ is measured. The measurement and signal processing to enable use of the relationship expressed in Equation No. 1 is discussed more fully below.

FIG. 2 exemplifies various aspects of an embodiment of a measuring circuit 18 that determines the volume of a drop falling between the parallel plates 42. In one aspect, the circuit 18 includes a resonant circuit 44 comprising a voltage controlled oscillator connected with the parallel plates 42. The resonant circuit 44 is configured to have a resonant frequency which is dependent on and can be altered by the capacitance of the parallel plates 42. In an initial condition—that is, in a condition without any drop between the plates—the capacitance of the parallel plates is $C_0$ and the resonant frequency of the resonant circuit 44 is $f_0$. Because the capacitor is made a part of the resonant circuit, any change, $\delta C$, in capacitance leads to a proportional change, $\delta f$, in the resonant frequency. This resulting change in frequency of the resonant circuit 44 may be measured by comparing its frequency with the fixed frequency of a phase locked loop circuit 46 which is tuned to have the same frequency, $f_0$, that the resonant circuit 44 has in its initial condition. The measured frequency change, $\delta f$, in the resonant circuit 44 may then be converted into a voltage which can be measured in an interpreting circuit 48. The interpreting circuit 48 is configured to convert the voltage information regarding the frequency change $\delta f$ in the resonant circuit into the correlative capacitance change, $\delta C$, of the plates according to the known mathematically described relationship, $$\frac{\delta C}{C_0} \approx -\frac{2\delta f}{f_0} \qquad \text{(Equation No. 2)}$$

The relationship expressed in Equation No. 2 is demonstrated more fully below.

The interpreting circuit 48 is further configured to convert the resulting information regarding the change in capacitance, $\delta C$, of the plates 42 into the volume of the fluid drop which caused the frequency change in the resonant circuit, according to the relationship expressed in Equation No. 1. Interpreting circuits that convert information in the form of frequency change into a voltage are known in the art and are not described further here.

In a further aspect of the embodiment shown in FIG. 2, the interpreting circuit 48 may pass its information to an integrating circuit 50 in which the volume of all drops that have fallen within a certain period are recorded and integrated, thus deriving the rate of fluid flow in the drip chamber 12. In yet a further aspect of the invention, the flow rate determined by the integrating circuit 50 may be fed to a flow adjustment circuit 52, which may set the fluid flow rate in the drip chamber 12 by changing the settings of the upstream or downstream flow control devices 22, 20 as applicable according to the measured flow rate. For example, if the measured flow rate is greater than that desired, the flow adjusting circuit 52 may reduce the flow rate accordingly, and if the rate is less than that desired, may increase it. In one embodiment, a memory 54 stores a selected rate of fluid flow and is connected to a processor that compares the stored rate of fluid flow to the measured flow rate and provides a flow control signal to the flow control devices 20, 22 based on the difference. The operation of integrating and flow adjusting circuits are well known in the art, and are not described here.

FIG. 3 exemplifies one embodiment of a resonant circuit 44 connected to a phase locked loop circuit 46 (FIG. 2) that together may be used to measure the change in capacitance of the capacitor defined by the parallel plates 42. The circuits shown in FIG. 3 exemplify how the parallel plates 42 may be incorporated into a resonant circuit 44 which is tuned by a voltage controlled oscillator ("VCO"). The measured frequency of the resonant circuit 44 is fed to a phase locked loop circuit 46 (FIG. 2), which compares its own fixed frequency with that of the resonant circuit 44. Any change in frequency of the resonant circuit, such as may be caused by a change in capacitance of the parallel plates 42, is detected and measured, and converted into a voltage, that may then be fed to an interpreting circuit 48 (FIG. 2) and an integrating circuit 50 (FIG. 2) such as have been previously described.

Referring now to the resonant circuit 44 (VCO) of FIG. 3 in more detail, the capacitor $C_1$ functions to isolate the DC control voltage applied to the $C_{2\text{-}VARICAP}$ from the oscillator and is large relative to the $C_{2\text{-}VARICAP}$ capacitance. The frequency determining components of this circuit are the inductor $L_{RES}$, the $C_{FO}$, the varicap, $C_2$, and the capacitance between the plates 42. The $C_{2\text{-}VARICAP}$ is a voltage-controlled capacitor and is back-biased. As the positive voltage is increased, the capacitance is decreased. Therefore, when a drop passes between the plates 42, the control voltage $V_{KVCO}$ is increased proportional to the increased capacitance between the plates 44 to cause the total capacitance to remain constant, and therefore the output frequency to remain constant. The series network of $L_1$ and $R_4$ serve to isolate the high frequency from the control voltage $V_{KVCO}$. Capacitor $C_{FO}$ serves as feedback from the collector to the emitter to sustain oscillation of the circuit. Capacitor $C_4$ matches the emitter output to subsequent circuits. $C_5$ is a typical bypass capacitor to assure a low impedance on the upper side of $L_{RES}$. Resistors $R_1$, $R_2$, and $R_3$ serve as bias for the transistor $Q_1$. Diode $D_1$ is added to provide temperature compensation to the transistor $Q_1$. Transistor $Q_1$ is a bipolar transistor with characteristics that enable it to oscillate at the desired frequencies.

In addition to the VCO, a phase locked loop ("PLL") circuit is used with a frequency reference to establish a constant output frequency of the VCO. Any attempt at deviation of the phase of the VCO will result in a change in $V_{KVCO}$ to bring the circuit back into frequency stability. An integrated circuit PLL that could be used is the Motorola MC145151-2. The VCO output, $F_{OUT}$ is divided down by a Fujitsu MB467 to reduce the $F_{OUT}$ to a range usable by the PLL integrated circuit.

Referring to the phase locked loop part of the circuit 46, the frequency standard used applies a known signal whose frequency is proportional to a multiple of the desired VCO frequency. If the desired VCO frequency is to be 120 MHz, then a divider of 12 would give an output frequency of 10 MHz. If the frequency standard is also 10 MHz, then the VCO will lock in frequency and phase to the standard. If something perturbs the resonant circuit within the VCO, the control voltage will be shifted so that the VCO will remain at the desired frequency. This control voltage, or error voltage can be seen as being proportional to the drop volume and is the output to the interpreting circuit 48.

The integrating circuit 48 is an analog-to-digital (A-to-D) converter converting the error voltage to a digital number that can be integrated in the integrating circuit 50 to control a flow adjusting circuit 52 or used simply to give a measure of total flow for calibration of auxiliary equipment.

In another embodiment of the present invention, the change in capacitance of the plates 42 caused by a drop 30 falling between them may be determined by using a balanced bridge circuit rather than the resonant circuit 44 and phase locked loop circuit 46 of the previous embodiment. However, the advantage of using a resonant circuit in combination with a phase locked loop circuit, as described in the previous embodiment, is that it allows a more precise reading of the change in capacitance of the plates than can be achieved with a balanced bridge circuit. The change in capacitance that will be caused by a fluid drop of the size typically occurring in an infusion set is very small, and will require a highly sensitive system to measure the change with accuracy. Capacitive bridge circuits are well known to those skilled in the art and no further description is provided here.

Although not intending to be bound by theory, the following is a more mathematical description of calculations enabling the determination of the volume of a drop. A pair of parallel plates has a capacitance, C, and has a small dielectric sphere introduced between them. A fixed charge, Q, is placed on the plates. It is known that the electric energy, W, stored on the plates may be expressed as a function of their capacitance, C, thus, $$W = \frac{Q^2}{2C} \quad \text{(Equation No. 3)}$$

Accordingly, the change in stored electric energy, $\delta W$, that results from a change in capacitance, $\delta C$, may be stated thus, $$\delta W \approx -\frac{Q^2}{2C^2}\delta C \quad \text{(Equation No. 4)}$$

or, $$dC \approx -\frac{2C^2}{Q^2}dW \approx -\frac{2}{V^2}dW \quad \text{(Equation No. 5)}$$

where $$V = \frac{Q}{C}$$

is the voltage on the capacitor.

It is further known that in the center of a parallel plate capacitor, the electric field, E, is approximately given by:

$$E \approx \frac{V}{d} \quad \text{(Equation No. 6)}$$

where d is the spacing between the parallel plates. Thus, $$\delta C = -\frac{2}{E^2 d^2}\delta W \quad \text{(Equation No. 7)}$$

From Stratton (J. A. Stratton, *Electromagnetic Theory*, McGraw Hill, 1941, page 206), it is known that the change in stored electric energy as a result of introducing a dielectric sphere into a uniform field, E, is given by $$\delta W = -\frac{2\pi r^3 (k-1)}{(k+2)}\varepsilon_0 E^2 \quad \text{(Equation No. 8)}$$

where r is the radius of the dielectric sphere, and $$k = \frac{\varepsilon}{\varepsilon_0}$$

is the dielectric constant of the sphere, which may also be stated as being the permittivity of the sphere $\in$ relative to the permittivity of free space, $\in_0 = 8.854 \times 10^{-12}$ Farads/meter.

Combining Equations Nos. 3 through 8, it is found that, $$\delta C \approx \frac{4\pi r^3 (k-1)}{d^2 (k+2)}\varepsilon_0 \quad \text{(Equation No. 9)}$$

However, since the drop of medication is an aqueous solution composed essentially of water, and the permittivity of water is between sixty and eighty, it is evident that the permittivity of water is large compared to the permittivity of free space. Therefore, since κ is much greater than unity under the physical structure of the device assumed here, the approximation:

$$\delta C \approx \frac{4\pi r^3}{d^2}\varepsilon_0 \quad \text{(Equation No. 10)}$$

follows from Equation No. 9 as a practical matter.

Since the volume of the spherical drop, $\Phi$, is related to the radius of the drop according to the expression $$\Phi = \frac{4\pi r^3}{3},$$

it follows that, $$\delta C \approx \frac{3\Phi\varepsilon_0}{d^2} \quad \text{(Equation No. 11)}$$

which is the expression set forth in Equation No. 1 above.

It will be apparent that two aspects of a change in capacitance of the parallel plates 42 as expressed in Equation No. 1 are particularly important. First, the change in capacitance is directly proportional to the volume of the drop 30. Second, the change in capacitance is insensitive to the dielectric constant of the drop.

Although these results were derived under the assumption of a spherical drop, experimental results for actual drops falling a short distance through parallel plates verify that Equation No. 1 is not sensitive to the variations from spherical that a drop typically experiences when falling a short distance.

The physical relationship expressed by Equation No. 2 reflecting the change in resonant frequency, $\delta f$, of a circuit that has a capacitor and which occurs when the capacitance of the capacitor changes by an amount $\delta C$ may be demonstrated as follows:

It is known that in a resonant L C circuit having a resonant frequency $f_0$, $$f_0 = \frac{1}{2\pi\sqrt{L_0 C_0}} \quad \text{(Equation No. 12)}$$

where $L_0$ is the known value of inductance and $C_0$ is the known value of capacitance incorporated into the L C circuit. Thus, a small change, $\delta f$, in $f_0$ is caused by a small change, $\delta C$, in $C_0$ according to the relationship, $$f_0 + \delta f = \frac{1}{2\pi\sqrt{L_0(C_0 + \delta C)}} \quad \text{(Equation No. 13)}$$

When $\delta C$ is small compared to $C_0$, as is the case in the present invention, then it follows that:

$$\frac{\delta C}{C_0} = -\frac{2\delta f}{f_0} \quad \text{(Equation No. 14)}$$

which is the expression set forth in Equation No. 2 above.

It will be appreciated by one of ordinary skill in the art that the above expressions of physical relationships used in determining the volume of a drop falling between parallel plates are approximations based on assumptions that result in a reasonable degree of accuracy. However, in practicing the present invention, it may be beneficial to calibrate the circuitry described as comprising measuring circuit 18 in order to initially set such circuitry to correctly measure the volume of a fluid drop of known volume. By so calibrating this circuitry, the practitioner of the invention may improve its accuracy in making subsequent measurements, as calibration may to some extent take into account factors (whether arising from the approximations or from physical qualities of a device built according to the principles of the invention) that might cause the measured volume of a drop to be larger or smaller than the actual volume of the drop.

While only the presently preferred embodiments have been described in detail, as will be apparent to those skilled in the art, modifications and improvements may be made to the device disclosed herein without departing from the scope of the invention. Accordingly, it is not intended that the invention be limited, except as by the appended claims.

We claim:

1. An apparatus for determining the volume of a fluid drop that moves through a predetermined path, comprising:

two plates forming a capacitor, the plates being separated by and positioned on either side of the predetermined path so that the fluid drop passes between the plates as it moves through the predetermined path thereby changing the capacitance of the capacitor;

a volume determining system connected to the capacitor configured to measure the amount of change in capacitance of the capacitor as the fluid drop moves through the predetermined path between the two opposing plates and configured to determine the volume of the fluid drop based on the amount of change of capacitance caused by the fluid drop moving between the two opposing plates.

2. The apparatus of claim 1 wherein the volume determining system comprises a resonant circuit having a resonance frequency determined by the capacitance of the capacitor formed by the two opposing plates and wherein a change in capacitance of the two opposing plates will result in a proportional change of the resonance frequency of the resonant circuit and the volume determining system is responsive to the resonance frequency to determine the volume of the fluid drop therefrom.

3. The apparatus of claim 2 wherein the volume determining system further includes an oscillator having a frequency of oscillation determined by the capacitance of the capacitor formed by the two opposing plates and the volume determining system is responsive to the oscillation frequency of the oscillator to determine the volume of the fluid drop therefrom.

4. The apparatus of claim 1 wherein the volume determining system comprises a capacitive balanced bridge coupled to the capacitor formed by the two opposing plates wherein a change in capacitance of the capacitor formed by the two opposing plates due to the fluid drop passing between the plates will unbalance the bridge and an unbalance signal will be provided by the bridge representative of the capacitance change and the volume determining system is responsive to the unbalance signal to determine the volume of the fluid drop therefrom.

5. The apparatus of claim 1 further comprising a drip chamber at which the two opposing plates are mounted with the drip chamber located between the two opposing plates, the drip chamber providing the predetermine path, wherein a fluid drop falling in the drip chamber between the plates will change the capacitance of the capacitor formed by the two opposing plates.

6. The apparatus of claim 5 wherein the volume determining system is further configured to integrate the individual determined volumes of the fluid drops passing between the two opposing plates over a selected period of time and provide a volume per unit time signal.

7. The apparatus of claim 6 further comprising a display connected to the volume determining circuit that receives the volume per unit time signal and displays a fluid flow rate based on the volume per unit time signal.

8. The apparatus of claim 6 further comprising:

a memory in which is stored a selected rate of fluid flow;

a processor connected to the memory and comparing the stored rate of fluid flow to the volume per unit time signal and providing a flow control signal based on the difference; and a flow control device responsive to the flow control signal to change the flow of fluid drops in response thereto.

9. The apparatus of claim 1 wherein the volume determining system is further configured to integrate the individual determined volumes of the fluid drops passing between the two opposing plates over a selected period of time and provide a volume per unit time signal.

10. The apparatus of claim 9 further comprising a display connected to the volume determining circuit that receives the volume per unit time signal and displays a fluid flow rate based on the volume per unit time signal.

11. The apparatus of claim 1 further comprising:

a memory in which is stored a selected rate of fluid flow;

a processor connected to the memory and comparing the stored rate of fluid flow to the volume per unit time signal and providing a flow control signal based on the difference; and a flow control device responsive to the flow control signal to change the flow of fluid drops in response thereto.

12. The apparatus of claim 1 wherein the plates are embedded in the wall of a drip chamber and the path is located between the plates within the drip chamber.

13. The apparatus of claim 1 wherein the plates are mounted to the exterior of the wall of a drip chamber and the path is located between the plates within the drip chamber.

14. An apparatus for determining the volume of a drop of medical fluid that moves through a predetermined path within a medical conduit having a wall, comprising:

two plates forming a capacitor, the plates being mounted to the wall of the conduit such that they are separated by and positioned on either side of the predetermined path so that the drop of medical fluid passes between the plates as it moves through the predetermined path thereby changing the capacitance of the capacitor;

a volume determining system connected to the capacitor configured to:

measure the amount of change in capacitance of the capacitor as the drop of medical fluid moves through the predetermined path in the medical conduit between the two opposing plates;

determine the volume of the fluid drop based on the amount of change of capacitance caused by the fluid drop moving between the two opposing plates; and integrate the individual determined volumes of the fluid drops passing between the two opposing plates over a selected period of time and provide a volume per unit time signal.

15. The apparatus of claim 14 further comprising a display connected to the volume determining circuit that receives the volume per unit time signal and displays a fluid flow rate based on the volume per unit time signal.

16. The apparatus of claim 15 further comprising:

a memory in which is stored a selected rate of fluid flow;

a processor connected to the memory and comparing the stored rate of fluid flow to the volume per unit time signal and providing a flow control signal based on the difference; and a flow control device responsive to the flow control signal to change the flow of fluid drops in response thereto.

17. A method for determining the volume of a fluid drop that moves through a predetermined path, comprising the steps of:

positioning two opposing plates defining a capacitor across the predetermined path so that the fluid drop passes between the two plates as it moves through the predetermined path, thereby changing the capacitance of the capacitor;

measuring the change in the capacitance of the capacitor as the fluid drop moves through the predetermined path between the two opposing plates; and determining the volume of the fluid drop based on the amount of change of capacitance caused by the fluid drop moving between the two opposing plates.

18. The method of claim 17 further comprising the step of changing the resonance frequency of a resonant circuit in response to the capacitance change caused by a fluid drop moving between the opposing plates;

wherein the step of determining the volume of the fluid drop further comprises determining the volume of the fluid drop based on the change in resonance frequency.

19. The method of claim 17 further comprising the step of changing the oscillation frequency of an oscillator in response to the capacitance change caused by a fluid drop moving between the opposing plates;

wherein the step of determining the volume of the fluid drop further comprises determining the volume of the fluid drop based on the change in oscillation frequency.

20. The method of claim 17 further comprising the step of unbalancing a capacitive balanced bridge circuit in response to the capacitance change caused by a fluid drop moving between the opposing plates;

wherein the step of determining the volume of the fluid drop further comprises determining the volume of the fluid drop based on the amount of unbalance of the bridge.

21. The method of claim 17 wherein the step of positioning two opposing plates defining a capacitor across the predetermined path comprises the step of positioning the two opposing plates across a drip chamber such that the drip chamber forms a part of the capacitor of the plates and wherein fluid drops that pass through the drip chamber pass between the two plates and change the capacitance of the capacitor formed by the two opposing plates.

22. The method of claim 21 further comprising the steps of:

integrating the individual determined volumes of the fluid drops passing between the two opposing plates over a selected period of time; and providing a volume per unit time signal.

23. The method of claim 22 further comprising the step of displaying a fluid flow rate in response to the volume per unit time signal.

24. The method of claim 22 further comprising the steps of:

storing a selected rate of fluid flow in a memory;

comparing the stored rate of fluid flow to the volume per unit time signal; and changing the flow of fluid drops in response thereto.

25. The method of claim 17 further comprising the steps of:
   integrating the individual determined volumes of the fluid drops passing between the two opposing plates over a selected period of time; and
   providing a volume per unit time signal.

26. The method of claim 25 further comprising the step of displaying a fluid flow rate in response to the volume per unit time signal.

27. The method of claim 25 further comprising the steps of:
   storing a selected rate of fluid flow in a memory;
   comparing the stored rate of fluid flow to the volume per unit time signal; and
   changing the flow of fluid drops in response thereto.

* * * * *